United States Patent [19]
Willingham

[11] Patent Number: 5,411,495
[45] Date of Patent: May 2, 1995

[54] SYSTEMS FOR RECEIVING AND STORING URINE FROM A FEMALE PATIENT

[76] Inventor: Clara J. Willingham, 1706 W. B St., Butner, N.C. 27509

[21] Appl. No.: 169,410

[22] Filed: Dec. 20, 1993

[51] Int. Cl.⁶ .............................................. A61F 5/44
[52] U.S. Cl. ................................... 604/329; 128/771; 604/327
[58] Field of Search ............................. 604/327–331; 128/760–772; 73/863.52

[56] References Cited

U.S. PATENT DOCUMENTS

| | | | |
|---|---|---|---|
| 3,894,845 | 7/1975 | McDonald | 128/762 |
| 4,661,100 | 4/1987 | Rechsteiner | 604/327 |
| 4,692,160 | 9/1987 | Nussbaumer | 604/331 |
| 4,795,449 | 1/1989 | Schneider et al. | 604/329 |
| 5,053,027 | 10/1991 | Manfredi | 604/327 |

*Primary Examiner*—David H. Willse
*Assistant Examiner*—Rob Clarke

[57] ABSTRACT

Systems for the receipt and storage of urine from a female patient comprising a pad formed of a liquid impervious material with a peripheral edge and an outwardly bowed recess interior of the periphery, the recess being positionable over the user and having an adhesive around the periphery for the securement of the pad in proper position, a forward strap extending forwardly and upwardly from the upper edge of the pad with a coupler at the upper end thereof and a pair of rearward straps extending upwardly to the lower back of the wearer, the pair of straps having upper ends, the bag having an opening at the lower end thereof; a belt positionable around the waist of a wearer with the rear straps attached at their upper end thereof to a rearward extent of the belt offset from the rear center thereof, the belt having a forward extent adapted to receive the coupler at the upper end of the forward strap, the belt having coupling means at the ends for securement of the belt and pad in position with respect to the user; a bag for the storage of urine received in the pad, the bag having an upper end with an upper opening and a lower end with a lower opening and a releasable cap, the bag having associated therewith a plurality of straps coupled with respect thereto for releasably securement around the leg of a user; and a tube extending from the opening at the lower end of the pad to the opening at the upper end of the bag for the passage to the bag of urine received in the pad for its storage and a one way valve in the tubing adjacent to the bag.

2 Claims, 4 Drawing Sheets

SYSTEMS FOR RECEIVING AND STORING URINE FROM A FEMALE PATIENT

BACKGROUND OF THE INVENTION

1. Field of the Invention

The present invention relates to systems for receiving and storing urine from a female patient and more particularly pertains to receiving the urine from a female patient in a pad and then storing the received urine in an associated bag.

2. Description of the Prior Art

The use of urine collection devices is known in the prior art. More specifically, urine collection devices heretofore devised and utilized for the purpose of receiving and storing urine are known to consist basically of familiar, expected, and obvious structural configurations, notwithstanding the myriad of designs encompassed by the crowded prior art which has been developed for the fulfillment of countless objectives and requirements.

The prior art discloses a large number of devices used for collecting and storing urine. By way of example, U.S. Pat. No. 4,846,817 to Mohr discloses an external urinary device for women.

U.S. Pat. No. 4,904,248 to Vaillancourt discloses a female incontinent urine collection device.

U.S. Pat. No. 4,955,879 to Mervine discloses an urinary drainage device.

U.S. Pat. No. 5,053,027 to Maxfredi discloses a female urine collection device.

Lastly, U.S. Pat. No. 5,146,637 to Bressler discloses a female urine collection apparatus.

In this respect, the systems for receiving and storing urine from a female patient according to the present invention substantially departs from the conventional concepts and designs of the prior art, and in doing so provides an apparatus primarily developed for the purpose of receiving the urine from a female patient in a pad and then storing the received urine in an associated bag.

Therefore, it can be appreciated that there exists a continuing need for new and improved systems for receiving and storing urine from a female patient which can be used for receiving the urine from a female patient in a pad and then storing the received urine in an associated bag. In this regard, the present invention substantially fulfills this need.

SUMMARY OF THE INVENTION

In view of the foregoing disadvantages inherent in the known types of urine collection devices now present in the prior art, the present invention provides an improved system for receiving and storing urine from a female patient. As such, the general purpose of the present invention, which will be described subsequently in greater detail, is to provide a new and improved system for receiving and storing urine from a female patient and method which has all the advantages of the prior art and none of the disadvantages.

To attain this, the present invention essentially comprises new and improved systems for the receipt and storage of urine from a female patient comprising a pad which is formed of a liquid impervious material with a peripheral edge and an outwardly bowed recess interior of the periphery. The recess is positionable over the female urethra and vagina and has an adhesive around the periphery for the securement of the pad in proper position. A forward strap extends forwardly and upwardly from the upper edge of the pad with a loop at the upper end thereof and a pair of rearward straps extending upwardly to the lower back of the wearer. The pair of straps have upper ends. The bag has an opening at the lower end thereof. A belt which is positionable around the waist of a wearer with the rear straps attached at their upper end thereof to a rearward extent of the belt is offset from the rear center thereof. The belt has a forward extent adapted to receive the loop at the upper end of the forward strap. The belt has releasable coupling means at the ends for securement of the belt and pad in position with respect to the user. A bag is provided for the storage of urine received in the pad. The bag has an upper end with an upper opening and a lower end with a lower opening and a releasable cap. The bag has associated therewith a plurality of straps coupled with respect thereto for releasably securement around the leg of a user. A tube extends from the opening at the lower end of the pad to the opening at the upper end of the bag for the passage to the bag of urine received in the pad for its storage and a one way valve in the tubing adjacent to the bag. A box is secured to the containing strips of litmus paper for contacting the collected and stored urine to determine its chemical composition.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent of legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide new and improved systems for receiving and storing urine from a female patient which have all the advantages of the prior art urine collection devices and none of the disadvantages.

It is another object of the present invention to provide new and improved systems for receiving and storing urine from a female patient which may be easily and efficiently manufactured and marketed.

It is a further object of the present invention to provide new and improved systems for receiving and storing urine from a female patient which are of durable and reliable constructions.

An even further object of the present invention is to provide new and improved systems for receiving and storing urine from a female patient which are susceptible of a low cost of manufacture with regard to both materials and labor, and which accordingly are then susceptible of low prices of sale to the consuming public, thereby making such systems for receiving and storing urine from a female patient economically available to the buying public.

Still yet another object of the present invention is to provide new and improved systems for receiving and storing urine from a female patient which provide in the apparatuses and methods of the prior art some of the advantages thereof, while simultaneously overcoming some of the disadvantages normally associated therewith.

Even still another object of the present invention is to receive the urine from a female patient in a pad and then storing the received urine in an associated bag.

Lastly, it is an object of the present invention to provide new and improved systems for the receipt and storage of urine from a female patient comprising a pad formed of a liquid impervious material with a peripheral edge and an outwardly bowed recess interior of the periphery, the recess being positionable over the user and having an adhesive around the periphery for the securement of the pad in proper position, a forward strap extending forwardly and upwardly from the upper edge of the pad with a coupler at the upper end thereof and a pair of rearward straps extending upwardly to the lower back of the wearer, the pair of straps having upper ends, the bag having an opening at the lower end thereof; a belt positionable around the waist of a wearer with the rear straps attached at their upper end thereof to a rearward extent of the belt offset from the rear center thereof, the belt having a forward extent adapted to receive the coupler at the upper end of the forward strap, the belt having coupling means at the ends for securement of the belt and pad in position with respect to the user; a bag for the storage of urine received in the pad, the bag having an upper end with an upper opening and a lower end with a lower opening and a releasable cap, the bag having associated therewith a plurality of straps coupled with respect thereto for releasably securement around the leg of a user; and a tube extending from the opening at the lower end of the pad to the opening at the upper end of the bag for the passage to the bag of urine received in the pad for its storage and a one way valve in the tubing adjacent to the bag.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts through the various Figures.

DESCRIPTION OF THE PREFERRED EMBODIMENT

Figure 1:
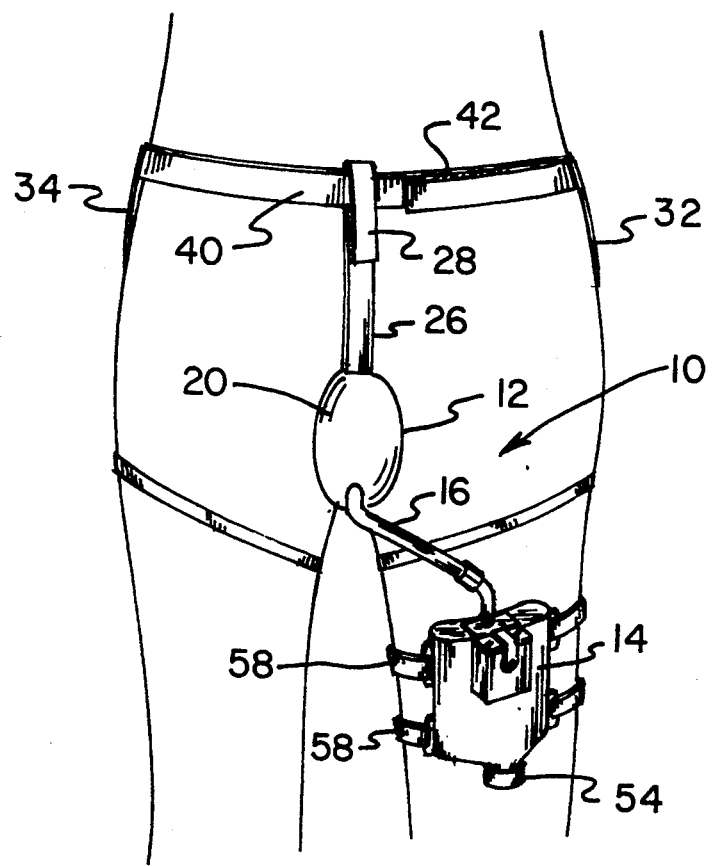
FIG. 1 is a perspective illustration of the preferred embodiment of the systems for receiving and storing urine from a female patient constructed in accordance with the principles of the present invention.
Figure 2:
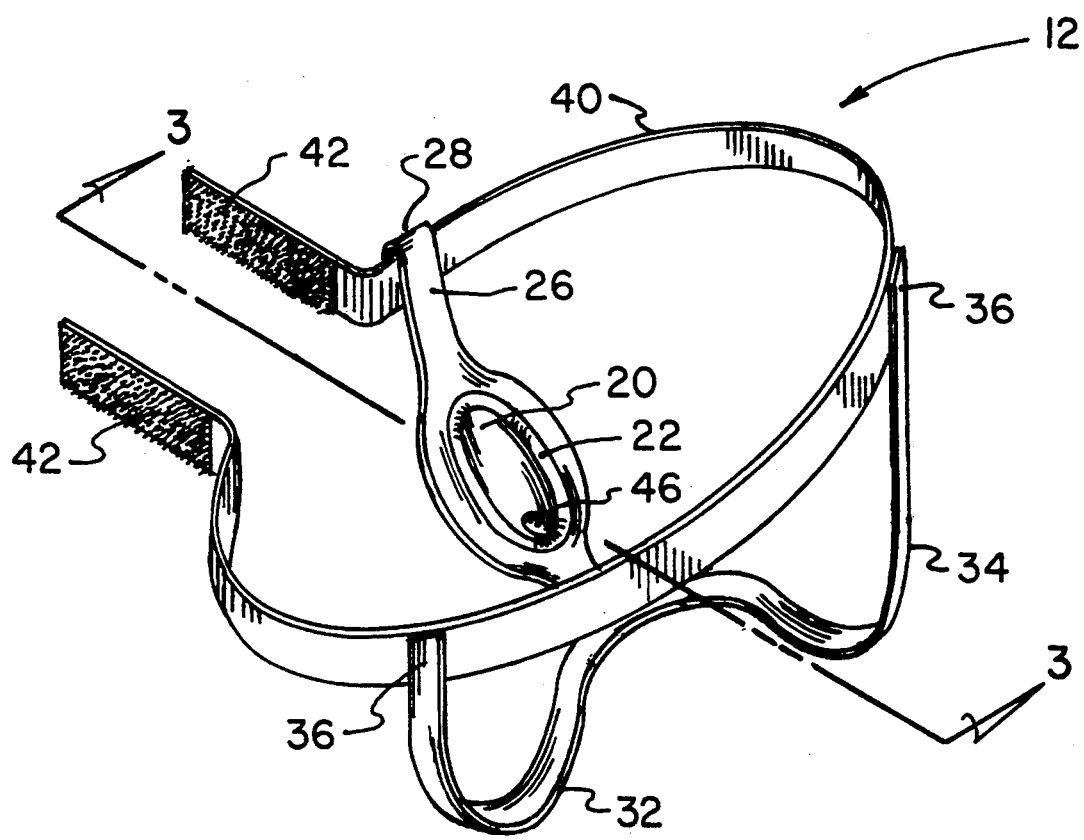
FIG. 2 is an enlarged perspective illustration of the pad portion of the system shown in FIG. 1.
Figure 3:
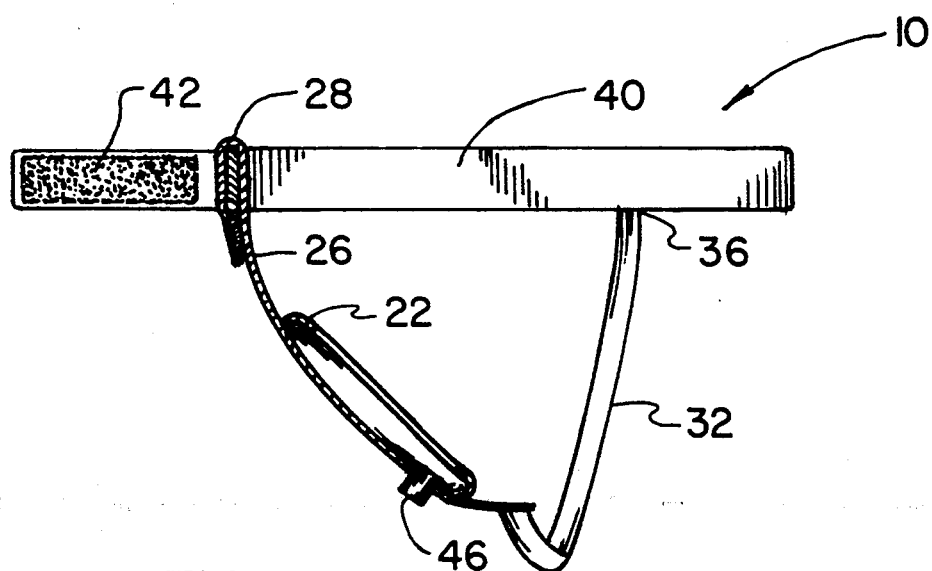
FIG. 3 is a cross sectional view of the device shown in FIG. 2 taken along line 3—3 of FIG. 2.
Figure 4:
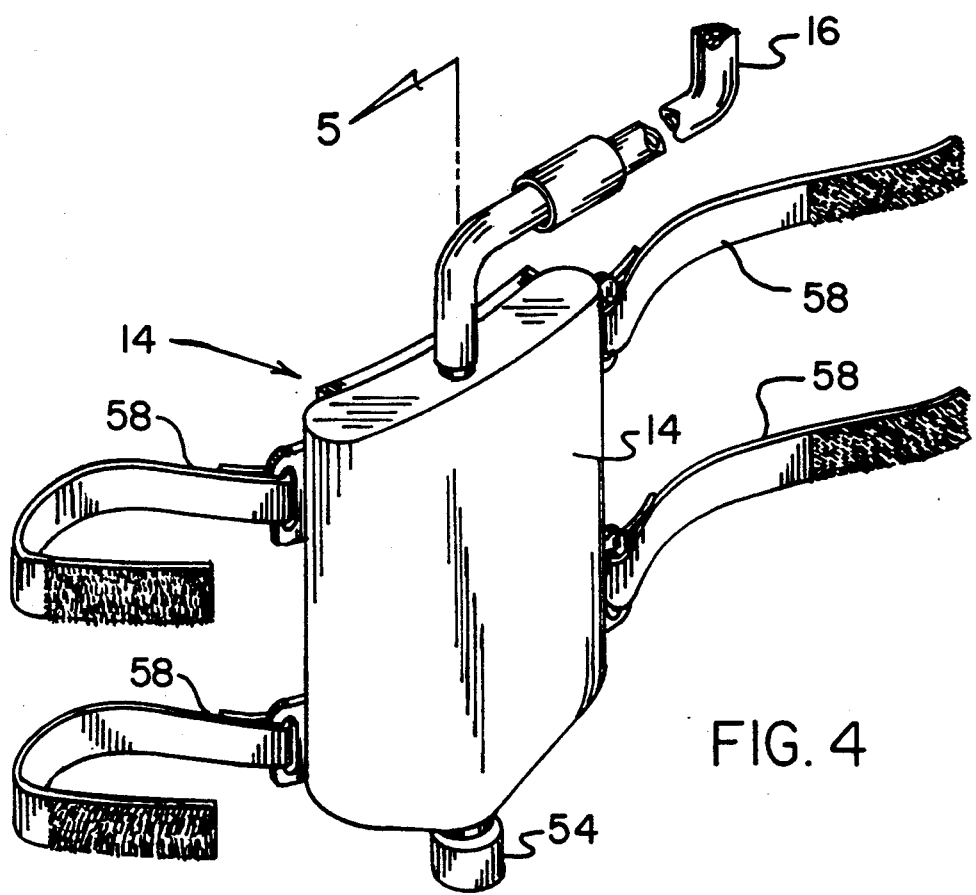
FIG. 4 is a perspective illustration of the bag portion of the system shown in FIG. 1.
Figure 5:
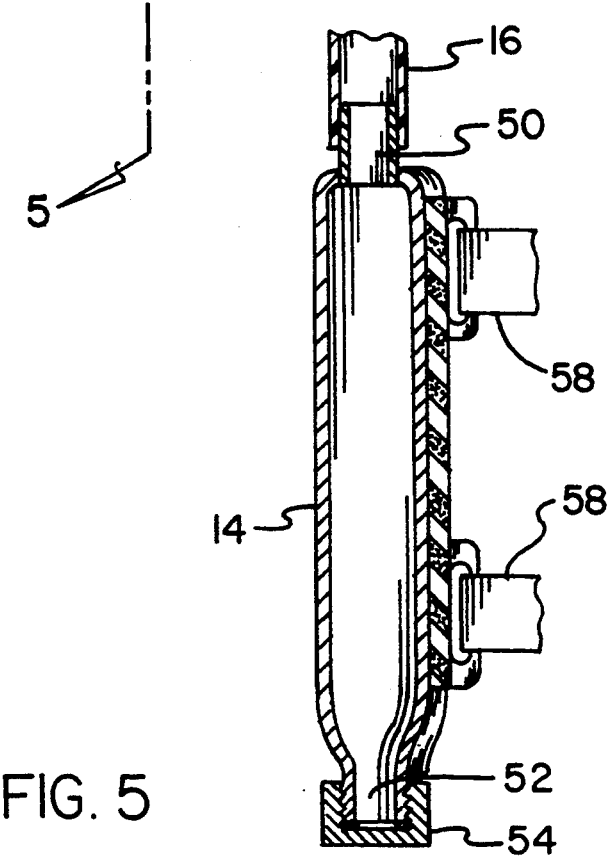
FIG. 5 is a cross sectional view of the device shown in FIG. 4 taken along line 5—5 of FIG. 4.
Figure 6:
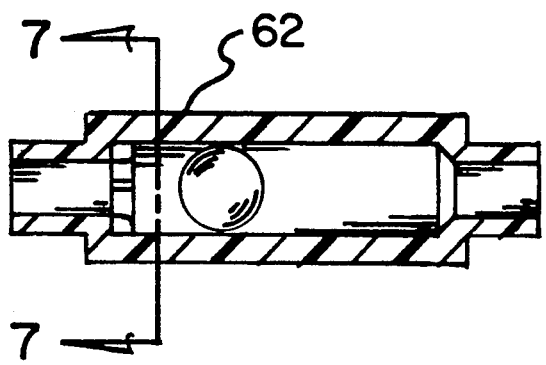
FIG. 6 is a cross sectional view of the valve shown above the bag in FIG. 4.
Figure 7:
FIG. 7 is a cross sectional view taken along line 7—7 of FIG. 6.

With reference now to the drawings, and in particular to FIG. 1 thereof, the preferred embodiment of the new and improved systems for receiving and storing urine from a female patient embodying the principles and concepts of the present invention and generally designated by the reference numeral 10 will be described.

Specifically, it will be noted in the various Figures that the invention includes a new and improved system 10 for the receipt and storage of urine from a female patient. In its broadest terms, the system 10 includes a pad 12, a bag 14 and a tube 16 coupled therebetween.

More specifically, the system includes a pad 12 formed of an essentially rigid liquid impervious material. The pad has a periphery with an outwardly bowed recess 20 within the periphery. The recess 20 is positionable over the female urethra and vagina with an adhesive 22 around the periphery for the securement of the pad in proper position for use.

A forward strap 26 extends forwardly and upwardly from the upper edge of the pad. It is formed with a loop 28 at the upper end thereof. A pair of rearward straps 32 and 34 extend upwardly to the lower back of the wearer. The rearward straps 32 and 34 have upper ends 36.

A belt 40 is positionable around the waist of a wearer. The rearward straps 32 and 34 are attached at their upper ends thereto to a rearward extent of the belt 40. The attachment is offset from the rear center extent of the belt 40. The belt has a forward extent adapted to centrally receive the loop 28 at the upper end of the forward strap. Releasable coupling means 42, preferably pile type fasteners, are located at the ends of the belt 40 for securement of the belt and pad in position with respect to the user. The pad also has an opening 46 at its lower end.

The next major component of the system 10 is a bag 14 formed as a rigid bottle. The bag functions for the storage of urine received in the pad 12. The bag 14 has an upper end with an upper opening 50 and a lower end with a lower opening 52. A releasable cap 54 is threadably received over the lower opening. The bag has associated therewith a plurality of straps 58. The straps 58 are coupled with respect to the bag 14 and function for the releasably securement of the bag 14 around the leg of a user.

A tube 16 extends from the opening 46 at the lower end of the pad to the opening 50 at the upper end of the bag 14. The tube 16 is for the passage of urine received in the pad to the bag for storage. A one way valve 62 is provided in the tubing 16 adjacent to the bag. The valve 62 precludes urine in the bag 14 and its odor from escaping.

Figure 9:
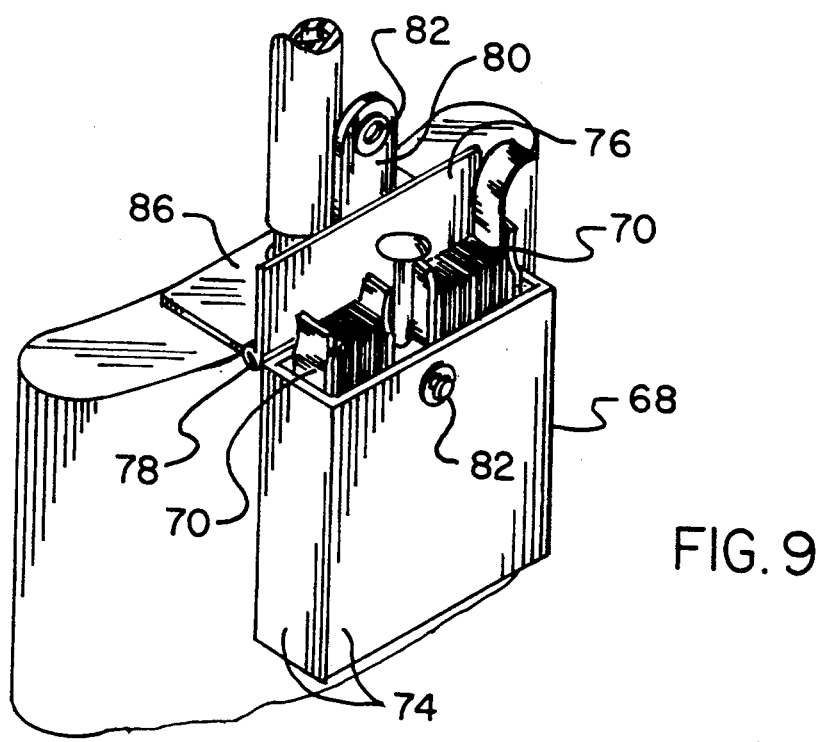
FIG. 9 is a perspective view of the device shown in Figure but with the lid open.
Figure 8:
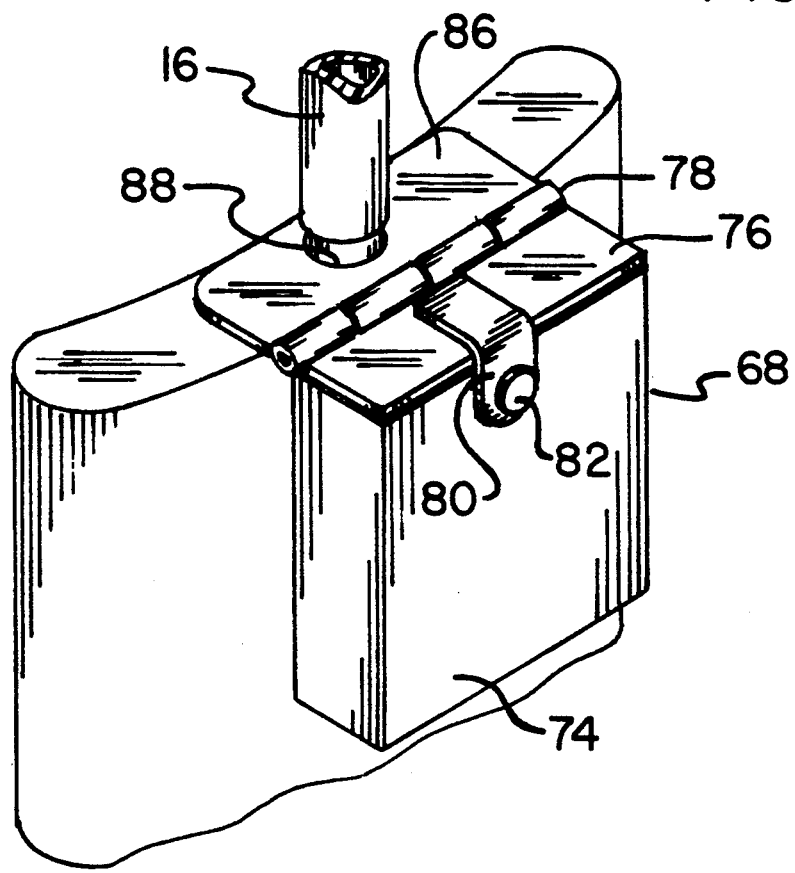
FIG. 8 is a perspective illustration of an alternate embodiment of the invention.

An alternate embodiment of the invention is disclosed in FIGS. 8 and 9. In such embodiment, there is provided a box 68. The box 68 is for containing strips 70 of litmus paper. The litmus paper strips are for contacting the collected and stored urine in order to determine its chemical composition. This is a health testing procedure which can be self applied. The box has rigid walls 74 and a lid 76 secured thereto by a hinge 78. A strap 80 with snaps 82 holds the lid shut. A rearward plate 86 is provided with an aperture 88 for receiving the tube 16 for securement purposes.

The present invention is a rubber or plastic pad that is applied to females to direct urine and drainage into a bag. It is used in place of catheters to avoid infections. It meets the needs of people who have experienced problems which make it very difficult for them to control the release from the bladder, and those who may be draining for various reasons. In most such case, the usual procedure is to insert a catheter into the patient and to direct the discharge into a drainage bag. This procedure is very convenient to the medical staff because it reduces the amount of attention required, but, invariably, infection sets in as a result of the invasion. Patients who have catheters inserted in them may likely develop a fever, indicating some form of infection has incurred. When the catheter is removed, the fever subsides quickly.

The present invention covers the female urethra and vagina and is held in place with an adhesive band. It sticks to the outside of the labia pubic area and the perineal area, replacing large diapers which are worn by adults. The present invention does not cover the anus and does not interfere with other functions. A tube from the pad extends down to a bag which is used to collect the discharge.

The present invention is the safest method that can be used to deal with such conditions. It is reliable and comfortable and very easy to apply and remove without causing any discomfort to the patient.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by LETTERS PATENT of the United States is as follows:

1. A new and improved system for the receipt and storage of urine from a female patient comprising, in combination:

a pad formed of a liquid impervious material with a peripheral edge and an outwardly bowed recess interior of the periphery, the recess being positionable over the female urethra and vagina and having an adhesive around the periphery for the securement of the pad in proper position, a forward strap extending forwardly and upwardly from the upper edge of the pad with a laterally shiftable loop at the upper end thereof and a pair of rearward straps individually attached to the pad at their lower extents and extending upwardly to the lower back of the wearer, the pair of straps having upper ends, the pad having an opening at the lower end thereof;

a belt positionable around the waist of a wearer with the rearward straps individually attached at their upper end thereof to a rearward extent of the belt offset from the rear center thereof, the belt having a forward extent adapted to receive the loop at the upper end of the forward strap for lateral shifting to permit adjustment, the belt having releasable coupling means at the ends for securement of the belt and pad in position with respect to the user;

a bag for the storage of urine received in the pad, the bag having an upper end with an upper opening and a lower end with a lower opening and a releasable cap, the bag having associated therewith a plurality of straps coupled with respect thereto for releasable securement around the front of a leg of a user; and a tube extending from the opening at the lower end of the pad to the opening at the upper end of the bag for the passage to the bag of urine received in the pad for its storage and a one way valve in the tubing adjacent to the bag.

2. The system as set forth in claim 1 and further including:

a box secured to the bag and strips of litmus paper, the box containing the strips of litmus paper for contacting the collected and stored urine to determine its chemical composition.

* * * * *